US006709583B2

(12) United States Patent
Anderson, Jr. et al.

(10) Patent No.: US 6,709,583 B2
(45) Date of Patent: Mar. 23, 2004

(54) CONTINUOUSLY REGENERATED AND INTEGRATED SUPPRESSOR AND DETECTOR FOR SUPPRESSED ION CHROMATOGRAPHY AND METHOD

(75) Inventors: James M. Anderson, Jr., Arlington Heights, IL (US); Raaidah Saari-Nordhaus, Lindenhurst, IL (US)

(73) Assignee: Alltech Associates, Inc., Deerfield, IL (US)

( * ) Notice: Subject to any disclaimer, the term of this patent is extended or adjusted under 35 U.S.C. 154(b) by 16 days.

(21) Appl. No.: 10/409,858

(22) Filed: Apr. 8, 2003

(65) Prior Publication Data

US 2003/0209494 A1 Nov. 13, 2003

Related U.S. Application Data

(60) Continuation of application No. 09/804,688, filed on Mar. 12, 2001, now abandoned, which is a division of application No. 09/073,652, filed on May 6, 1998, now Pat. No. 6,200,477.

(51) Int. Cl.[7] .............................................. B01D 15/08
(52) U.S. Cl. .................. 210/198.2; 210/96.1; 210/635; 210/638; 210/656; 210/659
(58) Field of Search ................................ 210/635, 638, 210/656, 662, 663, 198.2, 96.1; 204/524, 632; 73/61.55; 436/150, 161, 175

(56) References Cited

U.S. PATENT DOCUMENTS

| | | | |
|---|---|---|---|
| 3,897,213 A | 7/1975 | Stevens et al. | 210/198.2 |
| 3,920,397 A | 11/1975 | Small et al. | 210/198.2 |
| 3,925,019 A | 12/1975 | Small et al. | 210/198.2 |
| 3,926,559 A | 12/1975 | Stevens | 210/198.2 |
| 4,299,698 A | 11/1981 | Rak | 210/96.1 |
| 4,459,357 A | 7/1984 | Jansen | 210/656 |
| 4,751,004 A | 6/1988 | Stevens | 210/659 |
| 4,814,090 A | 3/1989 | Kunz | 210/96.1 |
| 4,847,598 A | 7/1989 | Tucci | 210/196.1 |
| 4,888,098 A | 12/1989 | Nyberg | 204/1 R |
| 4,952,126 A | 8/1990 | Hanaoka | 210/656 |
| 5,248,426 A | 9/1993 | Stillian | 210/635 |
| 5,346,605 A | 9/1994 | Wolcott | 204/412 |
| 5,352,360 A | 10/1994 | Stillian | 210/198.2 |
| 5,480,555 A | 1/1996 | Momber | 210/96.1 |
| 5,597,734 A | 1/1997 | Small | 210/656 |
| 5,633,171 A | 5/1997 | Small | 210/198.2 |
| 5,759,405 A | 6/1998 | Anderson | 210/656 |
| 5,914,025 A | 6/1999 | Small | 205/789 |
| 5,990,684 A | 11/1999 | Merrill | 324/439 |

Primary Examiner—Ernest G. Therkorn
(74) Attorney, Agent, or Firm—Brinks Hofer Gilson & Lione

(57) ABSTRACT

An integrated suppressor and detector for suppressed ion chromatography includes a stationary phase, a fluid flow path, at least first and second regeneration electrodes, and at least first and second sensor electrodes. Methods of suppressed ion chromatography using the integrated suppressor and detector are also described.

4 Claims, 4 Drawing Sheets

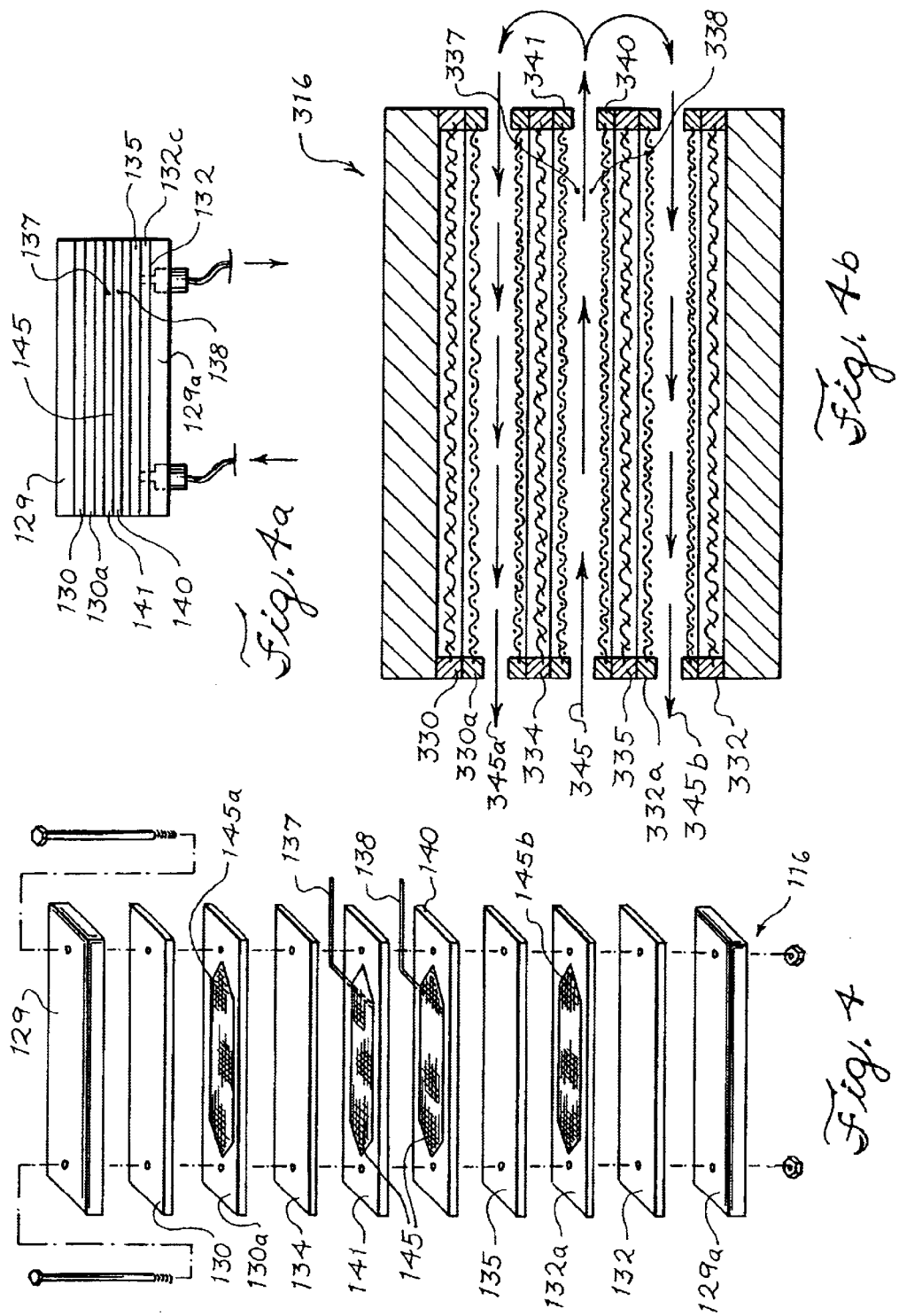

CONTINUOUSLY REGENERATED AND INTEGRATED SUPPRESSOR AND DETECTOR FOR SUPPRESSED ION CHROMATOGRAPHY AND METHOD

This application is a continuation of application No. 9/804,688, filed Mar. 12, 2001, now abandone, which is a divisional of application No. 09/073,652, filed May 6, 1998, now U.S. Pat. No. 6,200,477, which are hereby incorporated by reference herein.

FIELD OF THE INVENTION

The present invention relates to the field of ion chromatography (IC), and, in particular, to a continuously regenerated, integrated suppressor and detector for use in suppressed ion chromatography (SIC).

BACKGROUND OF THE INVENTION

Suppressed ion chromatography (SIC) is a commonly practiced method of ion chromatography which generally uses two ion-exchange columns in series followed by a flow through conductivity detector for detecting sample ions. The first column, called the analytical or separation column, separates the analyte ions in a sample by elution of the analyte ions through the column. The analyte ions are flowed through the analytical column via a mobile phase comprising electrolyte. Generally, a dilute acid or base in deionized water is used as the mobile phase. From the analytical column, the separated analyte ions and mobile phase are then flowed to the second column, which is called the suppressor or stripper. The suppressor serves two primary purposes: (1) it lowers the background conductance of the mobile phase by retaining (e.g., suppressing) the electrolyte of the mobile phase, and (2) it enhances the conductance of the analyte ions by converting the analyte ions to their relatively more conductive acid (in anion analysis) or base (in cation analysis). The combination of these two functions enhances the signal to noise ratio, and, thus, improves the detection of the analyte ions in the detector. Accordingly, upon exiting the suppressor, the analyte ions and suppressed mobile phase are then flowed to the detector for detection of the analyte ions. A variety of different types of suppressor devices and methods are discussed in U.S. Pat. Nos. 3,897,213; 3,920,397; 3,925,019; 3,926,559; and U.S. Ser. No. 08/911,847. Applicants hereby incorporate by reference the entire disclosure of these patent applications and patents.

As those skilled in the art will appreciate, both the mobile phase and the sample contain counterions of the analyte ions. A suppressor operates by ion exchange of suppressor ions, which are located in the suppressor, with both the (1) the mobile phase electrolyte counterions and (2) the sample counterions. In anion analysis, for example, the suppressor ions normally comprise hydronium ions and the mobile phase comprises electrolyte such as sodium hydroxide or mixtures of sodium carbonate and sodium bicarbonate. In cation analysis, the suppressor ions normally comprise hydroxide ions, and the mobile phase may comprise electrolytes such as hydrochloric acid or methanesulfonic acid. The suppressor ions are located on a stationary phase, which may be an ion exchange membrane or resin. As the mobile phase and sample (which contains both analyte ions and counterions of the analyte ions) are flowed through the stationary phase of the suppressor, the electrolyte counterions in the mobile phase and the sample counterions are retained on the stationary phase by ion exchange with the suppressor ions. When the suppressor ions are either hydronium or hydroxide, ion exchange of the electrolyte counterions with suppressor ions converts the mobile phase to water or carbonic acid, which are relatively non-conductive. On the other hand, the ion exchange of sample counterions with suppressor ions (i.e., hydronium or hydroxide ions) converts the analyte ions to their relatively more conductive acid (in anion analysis) or base (in cation analysis). Thus, the analyte ions, which are now in their relatively more conductive acid or base form, are more sensitive to detection against the less conductive background of the mobile phase.

However, unless the suppressor ions are continuously replenished during the suppression process, the concentration of suppressor ions on the stationary phase is reduced. Eventually the suppressor will become exhausted and its suppression capacity is either lost completely or significantly reduced. Thus, the suppressor must be either replaced or regenerated. The need to replace or regenerate the suppressor is inconvenient, may require an interruption in sample analysis, or require complex valving or regeneration techniques known in the art. One example of a known technique for regenerating a suppressor by continuously replenishing suppressor ions is disclosed in U.S. Pat. No. 5,352,360.

In addition to the need for regenerating or replacing suppressor ions, another problem associated with SIC is that a separate suppressor unit is usually required, and, therefore, the number of components in the system is increased over traditional IC systems. Traditional IC systems usually contain a mobile phase source, a pump, a sample injector, an analytical column and a detector for detecting the sample ions. In SIC, a separate suppressor unit is added to the system. This, in turn, increases the complexity of the system and also increases extra-column volume which may decrease chromatographic resolution and sensitivity. Therefore, it would also be advantageous to have a system of ion suppression chromatography which reduced the number of system components in traditional SIC systems.

Another problem associated with prior art SIC systems is that the mobile phase is converted to a weakly ionized form, which renders the mobile phase unsuitable for reuse. Thus, it would be advantageous if a system of SIC were developed in which the mobile phase is converted back to its strongly ionized form after suppression and, thus, may be reused.

SUMMARY OF THE INVENTION

In its various aspects, the present invention is capable of solving one or more of the foregoing problems associated with SIC.

In one aspect of the present invention, an integrated suppressor and detector is provided. By "suppressor" it is meant a device that is capable of converting the mobile phase to water or a weakly conductive form such as, for example, sodium carbonate or bicarbonate to carbonic acid and the ions to be detected (e.g. the analyte ions) to either their acid or base prior to detection. In this aspect of the invention, the suppressor is further equipped with sensor electrodes for detecting the analyte ions. By "integrated" it is meant that the suppressor and detector are contained within the same housing so that fluid transfer lines between a separately housed suppressor and detector are unnecessary.

In a further aspect of the invention, a method of suppression ion chromatography is provided wherein the suppressor is continuously regenerated during suppression. The suppressor comprises a stationary phase comprising suppressor ions which acts to suppress a mobile phase containing analyte ions to be detected. Electrolysis is performed on the mobile phase to produce regenerating ions. The regenerating ions are then flowed through the stationary phase to continuously replenish the suppressor ions lost during suppression. Preferably, electrolysis is performed on water present in the mobile phase.

In another aspect of the invention, an integrated suppressor and detector is provided. The integrated suppressor and detector comprises at least first and second regeneration electrodes and a fluid flow path extending between the first and second regeneration electrodes. A stationary phase comprising suppressor ions is positioned in the fluid flow path. The integrated suppressor and detector further comprises at least first and second sensor electrodes, in an electrical communication with a measuring device for recording analyte ions detected by the sensor electrodes.

In yet another aspect of the invention, a method of suppression ion chromatography is provided wherein the suppressed mobile phase is converted back to its strongly ionized state after suppression. Thus, the mobile phase is recycled and may be reused.

DESCRIPTION OF THE DRAWINGS

FIG. 2 is a cross-section view of integrated suppressor and detector according to one aspect of the invention taken along line 2—2 of FIG. 3a.

FIG. 3b is a cross-section view taken along line B—B of FIG. 3a.

FIG. 4 is an exploded perspective view of an integrated suppressor and detector according to another aspect of the invention.

FIG. 4a is a side view of an integrated suppressor and detector depicted in FIG. 4.

FIG. 4b is a cross-sectional view of an integrated suppressor and detector.

DETAILED DESCRIPTION OF THE PREFERRED EMBODIMENTS OF THE INVENTION

Figure 1:
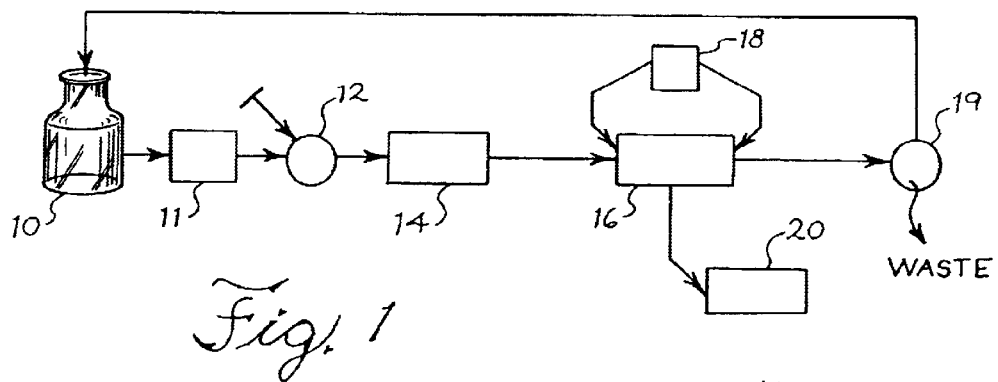
FIG. 1 is a schematic view of a suppressor ion chromatography system incorporating the integrated suppressor and detector of the invention.

FIG. 1 illustrates an IC system using the integrated suppressor and detector of the present invention. The IC system comprises a mobile phase source 10, a pump 11, a sample injector 12 and an analytical column 14, all in fluid communication. The pump 11, sample injector 12 and analytical column 14 may be selected from the variety of types known by those skilled in the art. For example, preferred pumps include the ALLTECH 526 pump available from ALLTECH ASSOCIATES, INC. (Deerfield, Ill.). Preferred analytical columns include the ALLTECH ALLSEP or UNIVERSAL CATION COLUMNS. Preferred sample injectors include the RHEODYNE 7725 injection valve.

An integrated suppressor and detector 16 in fluid communication with the analytical column 14 is further provided. As discussed below, the suppressor and detector 16 is connected to a power source 18 and a measuring device 20. Preferred power sources include the KENWOOD PR36-1.2A. A preferred measuring device is a conductivity detector such as the OAKTON ¼ DIN Conductivity and Resistivity Controllers (OAKTON 100 Series). Another suitable measuring device for use with the present invention is an electrochemical detector. The measuring device 20 measures or records the analyte ions detected by sensor electrodes in the integrated suppressor and detector 16.

In operation, the direction of fluid flow is as follows. The mobile phase is flowed from mobile phase source 10 by pump 11 through injection valve 12 to analytical column 14 to suppressor and detector 16. Upon exiting the suppressor and detector 16, the mobile phase is flowed through recycling valve 19, which directs fluid flow either to waste or back to mobile phase source 10 as discussed below. The recycling valve 19 is preferably a three-way valve.

Figure 2:
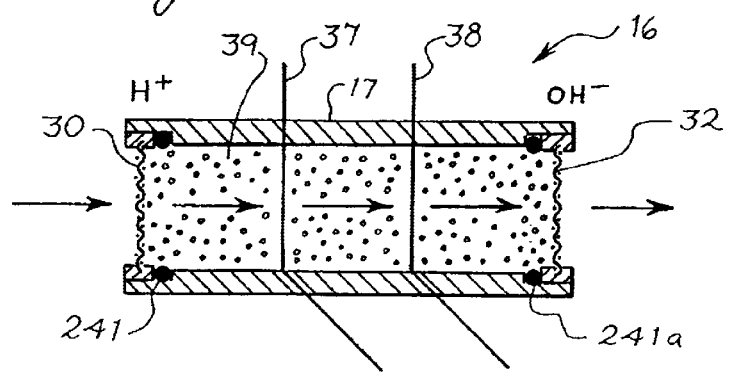

With reference to FIG. 2, the suppressor and detector 16 comprises a first regeneration electrode 30 and a second regeneration electrode 32. The regeneration electrodes are held in housing 17 of the suppressor and detector 16 by a threaded nut (not shown). Seals 241 and 241a are preferably included to provide a fluid-tight seal between electrodes 30 and 32 and housing 17. The seals 241 and 241a are preferably O-rings made from materials that are compatible with acids and bases such as, for example, ethylene propylene. Preferably, the regeneration electrodes are flow-through electrodes. By flow-through electrodes, it is meant that the electrodes allow sample analyte ions and mobile phase to flow therethrough. The electrodes are preferably made from carbon, platinum, titanium, stainless steel or any other suitable conductive, non-rusting material. The most preferred electrodes are made of platinum coated titanium, ruthenium oxide coated titanium, titanium nitride coated titanium, gold, or rhodium with an average pore size of between 0.1 $\mu$m and 100 $\mu$m. The first regeneration electrode 30 and the second regeneration electrode 32 are connected to the power source 18. A fluid flow path (indicated by arrows) is positioned between the first and second regeneration electrodes. The fluid flow path may preferably extend from the first regeneration electrode 30 to the second regeneration electrode 32. The fluid flow path may be defined by internal walls of housing 17. Housing 17 is preferably made from an inert material such as those disclosed in co-pending application Ser. No. 08/911,847. Also, as those skilled in the art will appreciate, the housing 17 should be constructed from a relatively non-conductive material.

A stationary phase 39 is positioned in the fluid flow path. The stationary phase 39 may comprise a variety of stationary phases known in the art for suppressors. Such stationary phases include membranes and ion exchange resins, for example. Preferably, the stationary phase comprises ion exchange resin. In anion analysis, cation exchange resin will be used. A preferred cation exchange resin is BIORAD AMINEX 50W-X12 (which is a sulfonated polystyrene divinylbenzene 200–400 mesh). Other suitable stationary phases include DUPONT NAFION ion-exchange beads and membranes and PUROLITE ion-exchange resins. During operation, the preferred cation exchange resin comprises exchangeable hydronium ions. In cation analysis, anion exchange resin will be used. A preferred anion exchange resin is BIORAD AMINEX AG1-X8 100–200 mesh (which is a quaternary amine polystyrene divinyl benzene). During operation, the preferred anion exchange resin comprises exchangeable hydroxide ions.

Figure 3A:
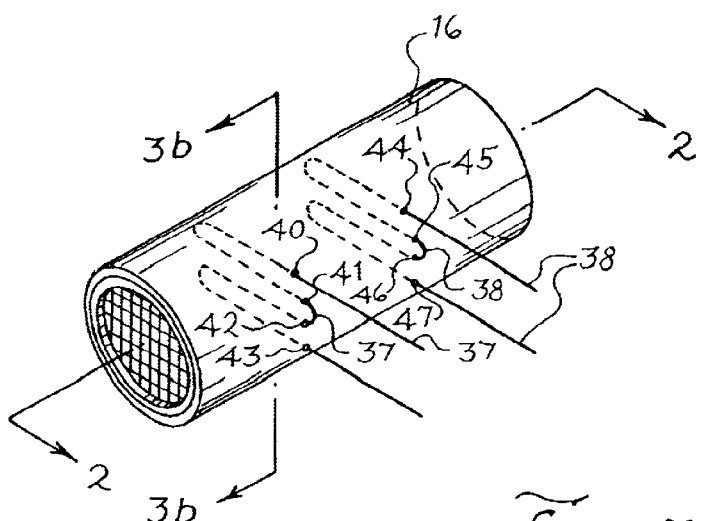
FIG. 3a is a side perspective view of an integrated suppressor and detector according to one aspect of the invention.
Figure 3B:
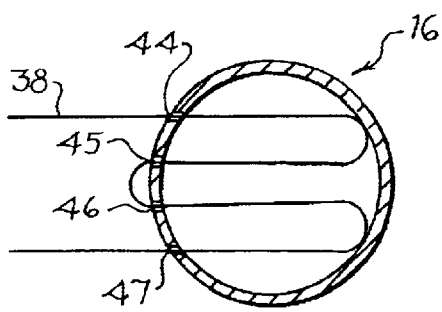

The suppressor and detector 16 also comprise at least two sensor electrodes for detecting the analyte ions. In the present embodiment, two sensor electrodes, first sensor electrode 37 and second sensor electrode 38 are shown. The first and second sensor electrodes are preferably located in the fluid flow path between first regeneration electrode 30 and second regeneration electrode 32. The first and second sensor electrodes preferably comprise either platinum wire or another electrochemically inert material such as gold, rheuthinium oxide or platinum, either neat or plated or suitable substrates such as titanium or stainless steel. The sensor electrodes 37 and 38 are preferably in electrical communication with a measuring device (not shown) for recording the analyte ions detected by the sensor electrodes. With reference to FIGS. 3a and 3b, the first and second sensor electrodes preferably have a serpentine configuration across a cross-section of the flow path. In particular, two rows of four holes each (see reference numerals 40–43 and 44–47, respectively) are provided. The first sensor electrode 37 is weaved through holes 40–43 and the second electrode 38 is weaved through holes 44–47 formed in housing 17. Most preferably, at least a portion of the stationary phase 39 will be positioned in the fluid flow path between the first and second sensor electrodes. Finally, an end of each of the first sensor electrode 37 and the second sensor electrode 38 is in electrical communication with the measuring device 20. Preferably, the suppressor and detector 16 is 21 mm×7.5 mm internal diameter. In a preferred aspect of the invention, the distance between the regeneration electrode 30 and sensor electrode is about 7.95 mm. The distance between regeneration electrode 32 and sensor electrode 38 is about 11.8 mm. The distance between sensor electrodes 37 and 38 is about 1.4 mm.

The system of the present invention may be used for detecting analyte ions comprising anions or cations. Moreover, a variety of mobile phases may be used. For cation analysis, preferred mobile phases include aqueous solutions of either hydrochloric acid, methanesulfonic acid or sulfuric acid. For anion analysis, preferred mobile phases include aqueous solutions of either sodium hydroxide or sodium carbonate/bicarbonate. Preferably, the mobile phase is aqueous and, therefore, no separate water-source is required. The operation of the suppressor and detector 16 will be described with reference to FIG. 2 for anion analysis and a mobile phase consisting of an aqueous solution of sodium hydroxide. As those of ordinary skill in the art will quickly appreciate, the invention may easily be adapted for cation analysis also.

To prepare the system for operation, the mobile phase should be flowed through the system and the power source turned on. Once the baseline created by the mobile phase has stabilized, the system is ready for ion analysis. A sample, which contains analyte anions to be detected and analyte counterions (e.g., cations), is injected at sample injector 12 and flowed to analytical column 14 by pump 11. The analyte anions are separated (or resolved) in analytical column 14 and then flowed with the mobile phase to suppressor and detector 16.

In anion analysis, the stationary phase 39 in the suppressor and detector 16 is preferably ion exchange resin comprising exchangeable hydronium ions. The sample which contains the previously separated analyte anions from analytical column 14 along with the analyte counter-cations are flowed with the mobile phase to the suppressor and detector 16. The analyte counter-cations are retained on the stationary phase 39 by ion exchange with the hydronium ions. Thus, the analyte ions are converted to their relatively more conductive acid according to the following formula:

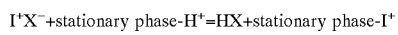

(where $X^-$ comprises analyte anions selected from, for example, Cl, $NO_2$, Br, etc.; and $I^+$ are analyte counterions selected from, for example, $K^+$). Also, the sodium ions in the mobile phase may be retained on the stationary phase 39 by ion exchange with the hydronium ions. Thus, the mobile phase is converted to the relatively non-conductive water according to the following formula:

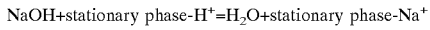

In addition to the foregoing reactions, a current is created across stationary phase 39, first regeneration electrode 30 and second regeneration electrode 32 by power source 18. The water from the aqueous mobile phase undergoes electrolysis to form regenerating ions at the first regeneration electrode 30 and second regeneration electrode 32, respectively. In anion analysis, the first regeneration electrode 30 is the anode at which regeneration ions consisting of hydronium ions are generated. The second regeneration electrode 32 is the cathode at which hydroxide ions are generated. As those skilled in the art will recognize, in cation analysis the polarity is reversed and the upstream regeneration electrode will be the cathode and the regenerating ions will comprise hydroxide ions.

In this embodiment, the regenerating hydronium ions generated at the first regeneration electrode 30 are then flowed through the stationary phase 39 thereby continuously regenerating the stationary phase 39 by ion exchange of the regenerating hydronium ions with the retained sodium ions and analyte counter-cations according to the following formulas:

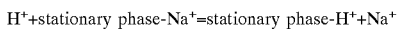

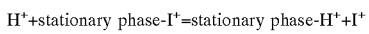

The sodium ions released from the stationary phase 39 are flowed to the second regeneration electrode 32 where they combine with the regeneration hydroxide ions to yield aqueous sodium hydroxide. If there are no analyte anions or analyte counter-cations flowing from the suppressor and detector 16, this aqueous sodium hydroxide may be flowed through recycling valve 19 and back to mobile phase source 10. In this fashion, a self-regenerating mobile phase is also provided. If, however, there are analyte anions or analyte counter-cations exiting the suppressor and detector 16 along with the aqueous sodium hydroxide, the fluid flow is preferably directed to waste. Preferably, the system will include a solvent recycling device, such as the ALLTECH SOLVENT RECYCLER 3000, which will sense the absence of analyte anions or analyte counter-cations and automatically direct the flow of the regenerated sodium hydroxide mobile phase to source 10. In contrast, if the solvent recycling device detects the presence of sample ions or counter-ions, it will direct the fluid flow to waste.

In a preferred embodiment of the invention, the analyte ions are detected while in the suppressor and detector 16. Still with reference to the anion analysis discussed above, there is a high concentration of hydronium ions proximate to sensor electrodes 37 and 38. The source of these hydronium ions are the regeneration hydronium ions generated at first regeneration electrode 30 and the hydronium ions released from the stationary phase 39 by ion exchange with the sodium ions and analyte counter-cations. Preferably, the concentration of hydronium ions is greater than the concentration of sodium ions or analyte counter-cations proximate the sensor electrodes. By optimizing the concentration of hydronium ions, the amount of sample ions in the acid form is likewise optimized, which leads to better detection sensitivity.

As discussed above, a current is applied across the stationary phase 39 for generating the regeneration ions. When the analyte anions in their acid form are flowed to the sensor electrodes, a change in the current is detected by the sensor electrodes. This change in current, and the extent of the change, reflects the amount of analyte ion present in the suppressor and detector 16. Preferably, the change in current is detected by a measuring device 20 and recorded.

In an alternate embodiment of the invention (not shown), the separate sensor electrodes may be omitted and the first and second regeneration electrodes 30 and 32 may also function as the sensor electrodes as previously described above. In yet another embodiment of the invention (not shown), one of the sensor electrodes may be omitted and one of the regeneration electrodes may perform the function of both a regeneration electrode and a sensor electrode as discussed above.

Another aspect of the invention using an ion-permeable ion exchange membrane is depicted in FIG. 4. FIG. 4 is an exploded view of an alternative configuration for the suppressor and detector. Suppressors using ion exchange membranes having this general configuration (except for the sensor electrodes) are known in the art. Examples of these suppressors are disclosed in U.S. Pat. Nos. 5,248,426 and 5,352,360, the disclosure of which are hereby incorporated by reference. In the embodiment depicted in FIG. 4, a first regeneration electrode 130 and a second regeneration electrode 132 are provided. The electrodes may be constructed from the same materials as previously discussed. However, as those of ordinary skill in the art will appreciate, the electrodes 130 and 132 preferably are not flow-through electrodes in this embodiment. First and second ion exchange membranes 134 and 135 are also provided. First and second ion exchange membranes preferably comprise exchangeable ions selected from the group consisting of hydronium and hydroxide ions. Positioned between ion exchanged membranes 134 and 135 and electrodes 130 and 132 are a first set of spacers 130*a* and 132*a*, which define fluid flow paths providing fluid communication between electrode 130 and membrane 134 and electrode 132 and membrane 135, respectively. Also, adjacent first and second ion exchange membranes are second set of spacers 140 and 141, respectively, which define a fluid flow path 145. The spacers 130*a*, 132*a*, 140 and 141 preferably may comprise a permeable, inert material such as a TEFLON membrane. Alternatively, the spacers may comprise an inert sheet constructed from MYLAR, PTFE, polypropylene or the like which has been cut to provide fluid communication between membranes 134 and 135 and the fluid flow path 145 as well as between electrodes 130 and 132 and membranes 134 and 135, respectively. Positioned in spacers 140 and 141 are sensor electrodes 137 and 138, respectively, which may be as previously described. Preferably, the sensor electrodes 137 and 138 are positioned at the downstream end of fluid flow path 145. As those skilled in the art will appreciate, the sensor electrodes will be positioned so that they are in fluid communication with the fluid flow path 145. Also, in the configuration depicted in FIG. 4, in addition to fluid flow path 145, fluid flow paths 145*a* and 145*b* are defined by the combination of spacer 130*a* and membrane 134 and spacer 132*a* and membrane 135, respectively.

In operation, the suppressor and detector depicted in FIG. 4 operates along the same general principles as previously discussed with respect to the embodiment depicted in FIGS. 1–3*b*. However, whereas the direction of current flow is generally parallel to the direction of fluid flow in the embodiment depicted in FIGS. 1–3*b*, the direction of current flow is generally perpendicular to the direction of fluid flow in the embodiment depicted in FIG. 4. Thus, in anion analysis, for example, the sample comprising analyte ions (anions) and sample counterions along with an aqueous mobile phase comprising electrolyte counterions are flowed to suppressor and detector 116 and fluid flow path 145. The water in the mobile phase undergoes electrolysis. In this embodiment, electrode 130 may be the anode and electrode 132 may be the cathode. Thus, hydronium ions are generated at electrode 130 and hydroxide ions are generated at the electrode 132. As the analyte ions and mobile phase are flowed through fluid flow path 145, the analyte counterions and mobile phase electrolyte counterions are retained on the membranes 134 and 135 by ion exchange with hydronium ions. The hydronium ions, both from the membranes 134 and 135 and the electrolysis product of water, migrate to fluid flow path 145 converting the analyte ions to their acid and the mobile phase to water. The analyte anions in their acid form may then be detected by sensor electrodes 137 and 138.

Additionally, the hydronium ions from the electrolysis will replace the retained electrolyte and sample counterions on membranes 134 and 135 thereby regenerating these membranes. The released electrolyte counterions may then recombine with the hydroxide ions generated by the electrolysis at electrode 132 to regenerate the mobile phase, which may be reused as described previously.

Although the sensor electrodes 137 and 138 may be positioned in one of the fluid flow paths 145, 145*a* or 145*b*, preferably, the sensor electrodes will be placed in path 145. Also, the sensor electrodes 137 and 138 are in electrical communication with a measuring device (not shown) for recording the detected analyte ions.

The devices and systems disclosed in U.S. Pat. Nos. 5,248,426 and 5,352,360 may be adapted for use according to yet another aspect of the invention. FIG. 4*b* shows a cross-section of a suppressor and detector 316 having the configuration of the suppressor and detector depicted in FIG. 4, except that the path of fluid flow through the suppressor and detector is modified. The electrodes 330 and 332, membranes 334 and 335 and spacers 330*a*, 332*a*, 340 and 341 may be as described with respect to FIG. 4. The sensor electrodes 337 and 338 are positioned in the fluid flow path 345. Preferably, the sensor electrodes are positioned towards the downstream end of fluid flow path 345. However, in this embodiment, the path of fluid flow is through fluid flow path 345 and then back through fluid flow paths 345*a* and 345*b* in a direction of flow opposite the direction of fluid flow through path 345.

With reference to FIG. 4*b*, in anion analysis, for example, an aqueous mobile phase comprising electrolyte is flowed through fluid flow path 345 to fluid flow paths 345*a* and 345*b* A sample comprising analyte anions and analyte counterions is flowed through fluid flow path 345. The analyte counterions are retained on membranes 334 and 335 by ion exchange with hydronium ions. Similarly, the mobile phase electrolytes are retained on membranes 334 and 335 by ion exchange with hydronium ions. The released hydronium ions from membranes 334 and 335 and the hydronium ions generated at electrode 330 from the electrolysis of water in the mobile phase combine with the analyte anions in the fluid flow path 345 forming the acid of the analyte anions and converting the mobile phase to water. The analyte anions, in their acid form, are then detected in the fluid flow path 345 by sensor electrodes 337 and 338, which are preferably in electrical communication with a measuring device (not shown).

The analyte anions (in their acid form) and water is then flowed to fluid flow paths 345a and 345b. This provides a continuous supply of water for the electrolysis. Also, the continuous supply of hydronium ions generated at electrode 330 replaces the retained sample and electrolyte counterions on membranes 334 and 335, thereby continuously regenerating these membranes. The displaced sample and electrolyte counterions (cations) migrate towards electrode 332 (where hydroxide ions are generated by the electrolysis) to flow path 345b and out of suppressor and detector 316. The effluent from flow paths 345a and 345b may be flowed to waste.

As those skilled in the art will appreciate, one of the spacers 140 and 141 (FIG. 4) or spacers 340 and 341 (FIG. 4b) may be eliminated. Thus, instead of two spacers, one spacer defining a fluid flow path 145 (FIG. 4) or 345 (FIG. 4b) may be used.

EXAMPLE 1

In this example, sample anions were analyzed according to a method of the invention using a suppressor and detector according to the embodiment of FIG. 2. The following items were used. The analytical column was an ALLTECH ALLSEP anion column, 100×4.6 mm ID packed with methacrylate-based quaternary amine anion exchange resin. The mobile phase was aqueous 0.7 mM sodium bicarbonate/ 1.2 mM sodium carbonate. The mobile phase flow rate was 0.5 mL/min. The integrated suppressor and detector was packed with high capacity polystyrene divinylbenzene based sulfonated cation exchange resin (BIORAD AMINEX 50W-X12 200–400 mesh). The integrated suppressor and detector was a column 21×7.5 mm ID. The distance between the inlet regenerating electrode and the first sensor electrode was 7.95 mm. The distance between the second sensor electrode and the outlet regenerating electrode was 11.8 mm. The distance between the first and second sensor electrodes was 1.4 mm. The conductivity detector was an OAKTON 1000 series ¼ DIN conductivity and resistivity controller. The power source was a KENWOOD PR 32-1.2A regulated DC power supply. The amount of current applied was 100 mA (corresponding voltage of 15 V).

Figure 5:
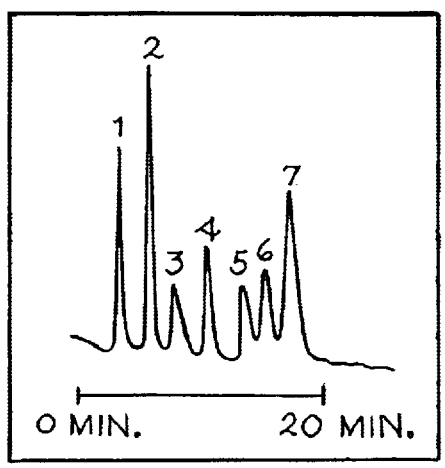
FIGS. 5–7 are chromatograms using an apparatus and method according to the invention and are referred to in the examples.

FIG. 5 is the chromatogram for a sample anion mixture (100 μL). The following peaks correspond to the following anions: 1—flouride (10 ppm); 2—chloride (20 ppm); 3—nitrite (20 ppm); 4—bromide (20 ppm); 5—nitrate (20 ppm); 6—phosphate (30 ppm); and 7—sulfate (30 ppm).

EXAMPLE 2

Figure 6:
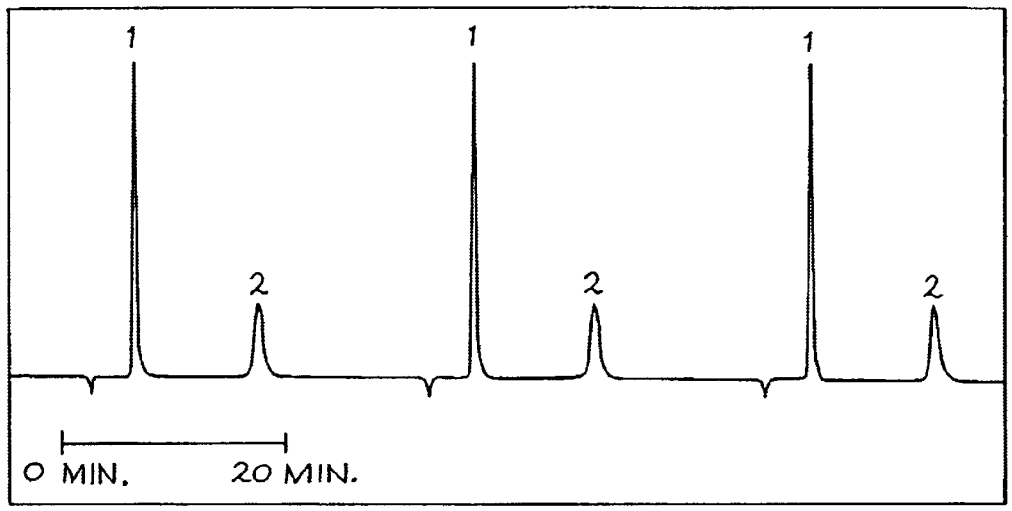

In this example, the same equipment and conditions as in Example 1 were used. FIG. 6 is the chromatogram for a sample anion mixture with three repetitive injections of 100 μL each. The following peaks correspond to the following anions: 1—chloride (10 ppm); and 2—sulfate (10 ppm).

EXAMPLE 3

In this example, sample cations were analyzed according to a method of the invention shown in the embodiment of FIG. 2. The following equipment and conditions were used. The analytical column was an ALLTECH Universal cation column, 100×4.6 mm ID, packed with silica coated with polybutadiene-maleic acid cation exchange resin. The mobile phase was aqueous 3.0 mM methane sulfonic acid. The mobile phase flow rate was 0.5 mL/min. The integrated suppressor and detector was packed with polystyrene divinyl benzene quaternary amine resin (BIORAD AMINEX AG-1-X8 100–200 mesh). The integrated suppressor and detector had the dimensions as set forth in Example 1. The conductivity detector was an OAKTON 1000 series ¼ DIN conductivity and resistivity controllers. A current of 200 mA was applied (corresponding voltage is 22 V).

Figure 7:
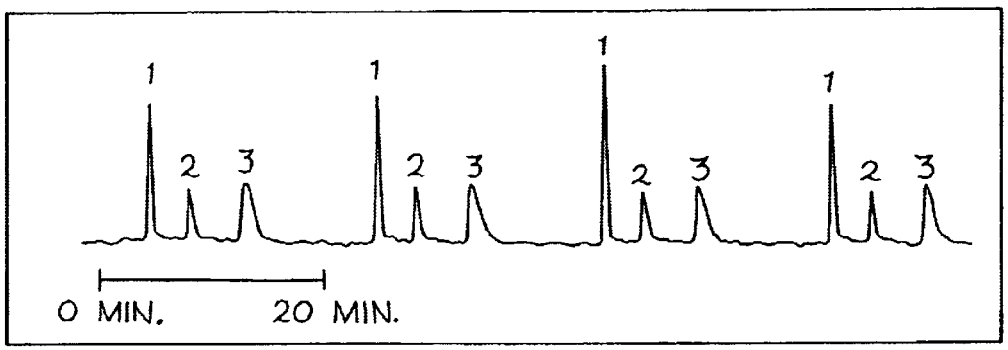

FIG. 7 is a chromatogram for a sample cation mixture, 4 repetitive injections of 100 μmL each. The following peaks correspond to the following cations: 1—lithium (1 ppm); 2—potassium (6 ppm); and 3—magnesium (6 ppm).

It should be understood that the foregoing description of the preferred embodiments and the examples are not intended to limit the scope of the invention. The invention is defined by the claims and any equivalents.

We claim:

1. An ion chromatography system comprising an integrated suppressor and detector for detecting analyte ions in a sample, the system comprising:

a) an analytical column; and b) a suppressor in fluid communication with the analytical column; wherein the suppressor comprises a first sensor electrode and a second sensor electrode for detecting the analyte ions.

2. The integrated suppressor and detector of claim 1 further comprising ion exchange resin.

3. The integrated suppressor and detector of claim 2 wherein at least a portion of the ion exchange resin is positioned between the first and second sensor electrodes.

4. The integrated suppressor and detector of claim 3 further comprising a fluid flow path wherein the first and second sensor electrodes are positioned in the fluid flow path.

* * * * *